(12) United States Patent
Miltenyi et al.

(10) Patent No.: US 8,747,290 B2
(45) Date of Patent: Jun. 10, 2014

(54) CENTRIFUGE FOR SEPARATING A SAMPLE INTO AT LEAST TWO COMPONENTS

(75) Inventors: Stefan Miltenyi, Bergisch Gladbach (DE); Winfried Schimmelpfennig, Krakow am See (DE); Holger Lantow, Rostock (DE); Niklas Elmar Neuschäfer, Rostock (DE); Martin Biehl, St. Wendel (DE); Eiad Kabaha, Bonn (DE); Jürgen Schulz, Jesteburg (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 760 days.

(21) Appl. No.: 12/745,689

(22) PCT Filed: Dec. 8, 2008

(86) PCT No.: PCT/IB2008/003845
§ 371 (c)(1),
(2), (4) Date: Aug. 20, 2010

(87) PCT Pub. No.: WO2009/072006
PCT Pub. Date: Jun. 11, 2009

(65) Prior Publication Data
US 2010/0311559 A1    Dec. 9, 2010

Related U.S. Application Data

(60) Provisional application No. 61/012,361, filed on Dec. 7, 2007.

(51) Int. Cl.
| | | |
|---|---|---|
| *B04B 1/12* | (2006.01) | |
| *B04B 7/08* | (2006.01) | |
| B04B 5/04 | (2006.01) | |
| B04B 13/00 | (2006.01) | |

(52) U.S. Cl.
CPC ... *B04B 7/08* (2013.01); *B04B 1/12* (2013.01); *B04B 2005/0464* (2013.01); *B04B 2013/006* (2013.01)
USPC .................................. 494/10; 494/43; 494/67

(58) Field of Classification Search
CPC .............. B04B 7/08; B04B 2005/0464; B04B 2013/006; B04B 1/12
USPC ............................... 494/5, 10, 43, 56, 64, 67
See application file for complete search history.

(56) References Cited

U.S. PATENT DOCUMENTS 3,586,413 A * 6/1971 Adams ............................ 494/18
3,955,755 A * 5/1976 Breillatt et al. .................. 494/10

(Continued)

FOREIGN PATENT DOCUMENTS

| EP | 0016552 A | 10/1980 |
| EP | 0 654 669 A | 5/1995 |

(Continued)

OTHER PUBLICATIONS

PCT Search Report dated Jun. 26, 2009 for application PCT/IB2008/003845.

(Continued)

*Primary Examiner* — Timothy Cleveland
(74) *Attorney, Agent, or Firm* — Kilpatrick Townsend & Stockton LLP (57) ABSTRACT

The invention relates to a centrifuge for separating a sample into at least two components, comprising a chamber for receiving a sample to be centrifuged. According to the invention, the centrifuge further comprises a means for controlling the progress of the sample separation is located at the chamber.

25 Claims, 11 Drawing Sheets

(56) References Cited

U.S. PATENT DOCUMENTS

| | | |
|---|---|---|
| 4,632,908 A | 12/1986 | Schultz |
| 5,260,598 A | 11/1993 | Brass et al. |
| 5,316,667 A | 5/1994 | Brown et al. |
| 5,691,208 A | 11/1997 | Miltenyi et al. |
| 5,904,840 A * | 5/1999 | DiBella .................. 494/10 |
| 6,080,581 A | 6/2000 | Anderson et al. |
| 6,709,377 B1 | 3/2004 | Rochat |
| 2002/0144939 A1 | 10/2002 | Dolecek |
| 2002/0173034 A1 | 11/2002 | Barbera-Guillem et al. |
| 2010/0311559 A1 | 12/2010 | Miltenyi et al. |

FOREIGN PATENT DOCUMENTS

| | | |
|---|---|---|
| EP | 0654669 A | 5/1995 |
| EP | 2227334 B1 | 10/2011 |
| WO | 90/04019 A | 4/1990 |

OTHER PUBLICATIONS

PCT Search Report dated Jul. 30, 2009 for application PCT/IB2008/003823.

* cited by examiner

CENTRIFUGE FOR SEPARATING A SAMPLE INTO AT LEAST TWO COMPONENTS

The invention relates to a centrifuge for separating a sample into at least two components and to a method for separating a sample into at least two components in which this centrifuge is used.

BACKGROUND OF THE INVENTION

A centrifugation can be used in a physical method to separate a sample into at least two of its components. In particular, centrifugation is used in the art to separate samples of biological origin into two or more components. These components can then separately be further processed.

When performing a centrifugation, it is advantageous to be able to monitor the progress of the separation of the components that the sample consists of.

Accordingly, the problem underlying the present invention was to provide a means of performing a centrifugation that allowed for monitoring the progress of the separation process.

BRIEF SUMMARY OF THE INVENTION

The problem underlying the present invention is solved both by a centrifuge and a method of using this centrifuge, both as described herein.

In one aspect of the invention, a centrifuge for separating a sample into at least two components is provided. Such a centrifuge comprises a chamber (or processing chamber or rotating container) for receiving a sample to be centrifuged and a means for controlling the progress of the sample separation located at the chamber. The separation of the sample results in at least a first component and a second component that are separated from each other. The components therefore form layers in the centrifuge chamber that can be detected.

In a preferred embodiment of the invention, the means for controlling the progress of the sample separation is a window, a mirror or a prism that is located such that light from a light source can be transmitted through at least a part of the sample and that the light leaving the prism is detectable by a light detector. Further, the means for controlling the progress of the sample separation can be a double prism, with two prism sections aligned in a mirror symmetrical fashion.

The chamber of the centrifuge comprises a circular base plate, the center of which is oriented substantially perpendicular to a rotational axis; a cladding or wall which is oriented substantially perpendicular to the base plate such that base plate and cladding together form a pot-like structure (lower portion of the chamber); and a circular cover plate (lid; upper portion of the chamber), which is positionable on the edge of the cladding that is remote from or opposite the base plate and the center of which is oriented substantially perpendicular to the rotational axis. Thereby, a closed centrifugation chamber is formed, consisting of a pot-like bottom part and an upper part in the form of a lid.

In one embodiment, the means for controlling the progress of the sample separation is positioned at the base plate or the cover plate of the chamber. It is preferred that the means for controlling the progress of the sample separation (e.g. the prism or double prism) is positioned at the cover plate of the chamber.

The means for controlling the progress of the sample separation is preferably positioned at a channel or at a gap which is located in the base plate or the cover plate of the chamber such that the sample can enter the channel or gap during the centrifugation such that the sample becomes detectable. In other words, the channel or gap is configured such that at least a part of the sample can flow into it during centrifugation. In particular, the separation of the sample becomes detectable, since light can at least in part penetrate the different components of the sample. Thereby, a signal is generated that allows for determining when the sample separation is complete. In addition, the chamber can comprise an outlet opening that allows for a component of the sample to be drained from the chamber during centrifugation.

Besides the formation of layers, the separation of the sample can also be detected using the pH value and/or temperature. This will be explained in more detail with reference to the figures.

Preferably, the channel is oriented such that it stretches radially in a linear fashion from an area located at the rotation axis to an area located at a perimeter of the base plate or the cover plate, depending on where the detection means is located. The channel is positioned such that at either side light can pass from the prism or double prism into the channel which holds sample during centrifugation. The detection of the light passing through the sample allows for determining how far the separation of the sample has proceeded and also for determining the position of the borders between different components of the sample. Based on the knowledge of the position of the borders between different components, it becomes possible to drain certain components from the chamber through at least one outlet port, which is located at the chamber.

In a preferred embodiment, the chamber is configured such that it can serve as or accommodate a container for the cultivation of cells. Thereby, the centrifugation chamber can be used both for cell culture purposes and for processing of the cells grown therein. The chamber allows a large range of cell culture methods to be performed, such as growing of cells, separating, washing, enriching the cells or different kinds of cells, or others. For this purpose, the chamber may comprise further inlet/outlet openings, e.g. for gas, cell culture media or alike. Cell culture conditions are known in the art.

In another aspect of the invention, a method for separating a sample into at least two components is provided. Such a method comprises the steps of providing a sample, and centrifuging the sample in a centrifuge as described above and herein.

As described above and herein, the sample is preferably a biological sample, such as blood, bone marrow, cells, compositions comprising cells or cellular components or alike.

The centrifuge can be part of a sample processing unit. This sample processing unit, may comprise an input port and an output port coupled to centrifuge chamber as described herein having at least one sample chamber, wherein the sample processing unit is configured to provide a first processing step to a sample or to rotate the container so as to apply a centrifugal force to a sample deposited in the chamber and separate at least a first component and a second component of the deposited sample. The sample processing unit can be coupled to a sample separation unit to form a system. The sample separation unit can be coupled to the output port of the sample processing unit, wherein the sample separation unit comprises a separation column holder, a pump, and a plurality of valves configured to at least partially control fluid flow through a fluid circuitry and a separation column positioned in the holder, wherein the separation column is configured to separate labeled and unlabeled components of sample flowed through the column.

DETAILED DESCRIPTION OF THE INVENTION

The present invention provides a centrifuge for separating a sample into at least two components. Such a centrifuge comprises a chamber or processing chamber for receiving a sample to be centrifuged and a means for controlling the progress of the sample separation is located at the chamber.

The sample chamber or chamber, which may also be part of a processing unit (see below), is now further described with reference to FIGS. 1 through 4.

Figure 1:
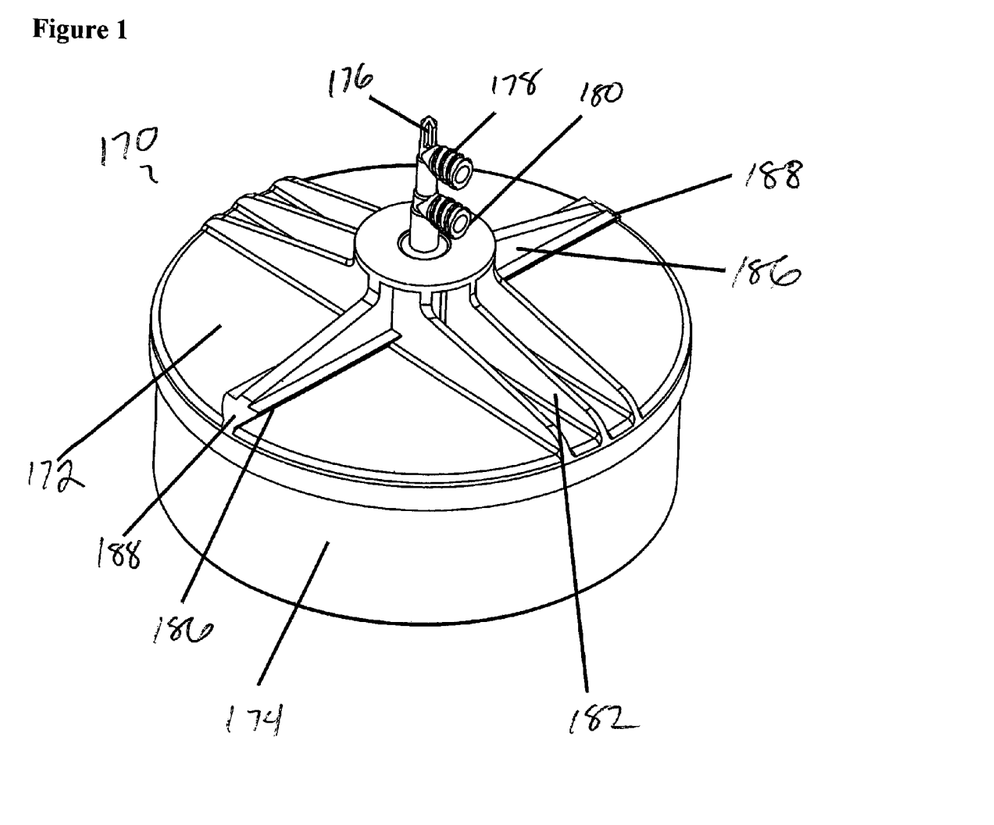
FIG. 1 illustrates a chamber of a centrifuge, according to an embodiment of the present invention.

A processing chamber of a centrifuge according to an embodiment of the present invention is described with reference to FIG. 1. The chamber 170 includes an upper portion 172 and a lower portion 174, with a rotational axis 176 and fluid ports or line connect 176, 178 fluidly connected to one or more internal compartments of the chamber 170. The upper portion 172 includes a support structure 182 that is oriented substantially radially, stretching from an area located at the rotation axis 176 to an area located at a perimeter of the upper portion 172, as well as structure 184 including a channel 186 that can include at least a portion that is visible through a window or prism 188. The channel 186 can be fluidly coupled to a sample containment compartment in the chamber 170 and configured for external monitoring or detection of sample processing. For example, a component (e.g., cells) in fluid in the channel 186 may become visibly separated during processing steps, thereby indicating separation of cells or sample components in one or more internal compartments of the chamber. Rotational means or bearing 180 provides rotational movement of the chamber 170 about the axis 176.

The chamber 170 may further comprise at least one vent, preferentially comprising a sterile, hydrophobic membrane or tampon. Preferably, these membranes or tampons may be located at the top or bottom of the chamber. The at least one vent in the chamber has the particular advantage that the volume in the chamber can be changed easily without changing the pressure in the chamber or providing further inlet and/or outlet ports for the exchange of air or gas.

The centrifuges known in the art allow batch-wise centrifugation, i.e. if the volume of the sample to be reduced or concentrated is larger than the chamber, several centrifugation steps are necessary to receive the concentrated product. In one embodiment of the present invention the system allows continuous centrifugation: sample, media, gases and other materials can enter and leave the system e.g. through inlet and outlet ports (e.g. FIG. 1: inlet port 178 and outlet port 180) without stopping the centrifugation process and refilling the centrifuge (batch-wise centrifugation). This allows a continuous concentration of the sample and the product may be removed only once at the end of the centrifugation, thus avoiding potential contamination due to additional handling.

Figure 1A:
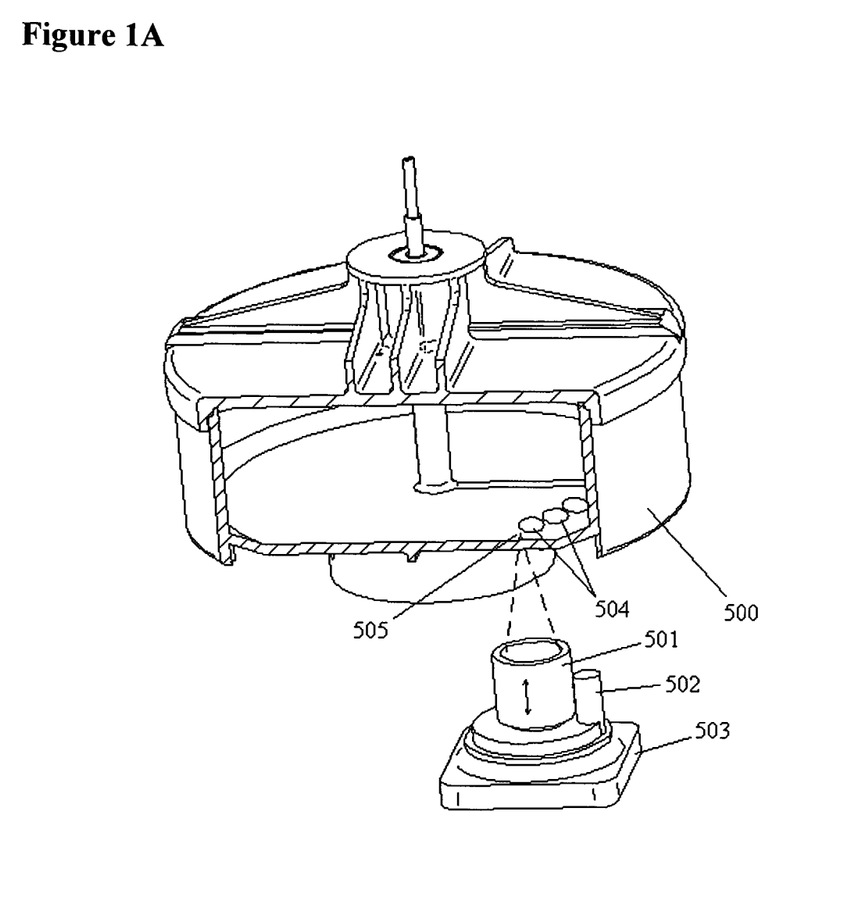
FIG. 1A illustrates a chamber of a centrifuge according to an embodiment of the present invention with a light source and a detector for detecting the progress of the sample separation in the chamber.

In FIG. 1a, a rotating container or centrifugation chamber 500 is shown. At the bottom of the rotating chamber 500 a microscope focus area 505 is positioned which comprises at least one sensor pad 504. Below the rotating chamber 500, a microscope camera module 503 is located that comprises a microscope optics 501 and a microscope drive motor 502 for focusing the optics. The microscope optics 501 is configured such that is can focus automatically to detect the sample that is being separated into at least two components during centrifugation. Thereby, the microscope camera module 503 can be used to detect different layers formed by the separated sample in the chamber 500 due to centrifugal forces. In addition, the pH value of the sample components can be measured. For this purpose, an indicator is used in the chamber 500 that changes its color dependent on the pH value that is present. Moreover, it is possible that the temperature of the sample in the chamber be measured using liquid crystals that are position in the chamber such that their position can be detected with a microscope camera module 503 from the outside. Thereby, the temperature in the chamber 500 can be determined.

The microscope camera module 503 can be mounted in a movable fashion, such that the module 503 can be directed with its microscope optics 501 at different sensor pads 504 located in the wall of the chamber 500. This facilitates the detection of various layers formed in the chamber 500 or the detection of the pH or the temperature at different positions within the chamber 500.

Figure 2:
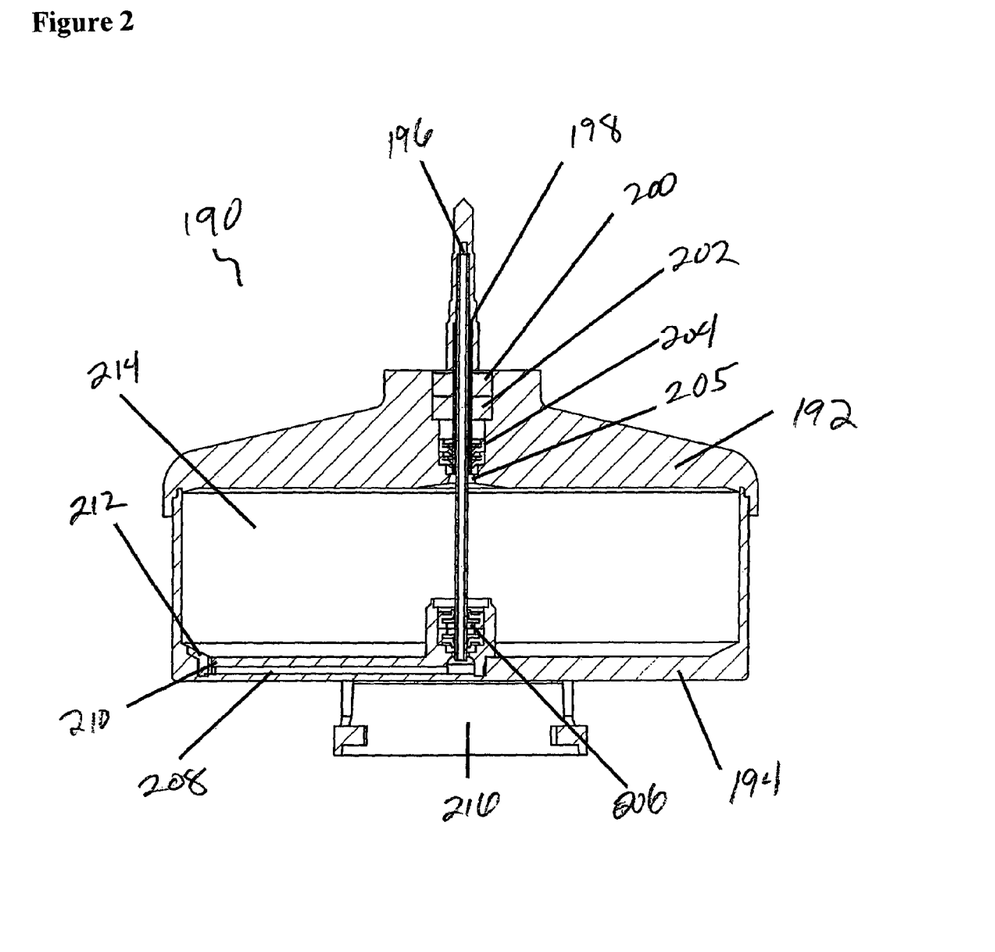
FIG. 2 shows a cross-sectional view of a processing chamber of a centrifuge, according to an embodiment of the present invention.

FIG. 2 illustrates a cross-sectional view of a sample processing chamber according to an embodiment of the present invention. The chamber 190 includes an upper portion 192 and a base portion 194, and one or more internal compartments. The chamber 190 is configured to rotate about an axis so as to apply a centrifugal force to sample disposed in one or more compartments in the chamber, thereby separating at least two components of the sample. The chamber includes central line 196 fluidly connected to at least one compartment of the chamber. Components of the chamber 190 further include outer line 198; rotational bearing 200, rotational seals 202, 204, 206; outer entry line to the chamber 205; lower radial channel 208; inner line entry 210 to a chamber compartment; slant 212, and deflector 214. Chamber retainer 216 is included and configured for secure positioning/coupling of the chamber 190 with other components of a system of the invention.

The centrifugation chamber 190 preferably comprises a rotating seal, optionally with two fluid lines, preferably with two fluid lines. The fluid lines can enter the chamber 190 at different position. For example, it is possible to position a first fluid line at the outer perimeter of the upper portion 192 (lid). A second fluid line could be positioned further inward, e.g. 2 mm to 20 mm further towards the center of the chamber 190. Optionally, a vent can be located at the upper portion 192, e.g. in the form of a membrane.

Generally, the position of openings such as holes or line entries in the centrifugation chamber can be configured such that they are best suited for the centrifugation of a particular sample. Depending on the components of a particular sample, and the relative volume of each component in the sample, the openings can be positioned so that the removal and/or detection of a particular component can be achieved.

Figure 2A:
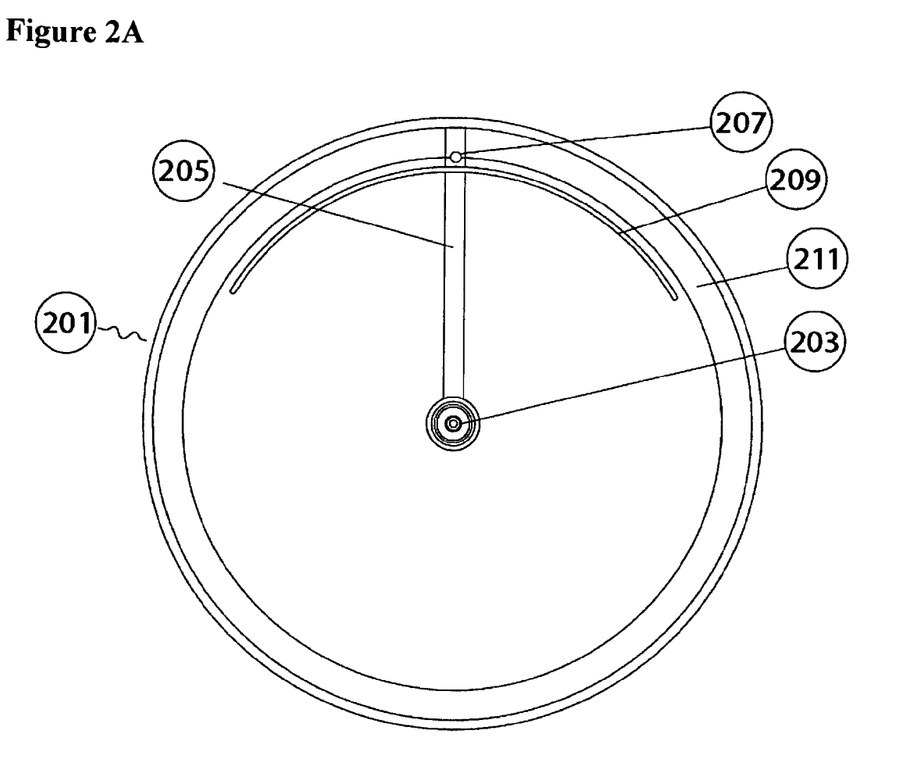
FIG. 2A illustrates a top plan view of a processing chamber, according to an embodiment of the present invention.

FIG. 2A illustrates a top plan view of a chamber 201. The chamber 201 includes an inner line 203, lower radial channel 205, inner line entry 207 to the chamber, optionally a deflector 209, slant 211 and a light pass.

Figure 3:
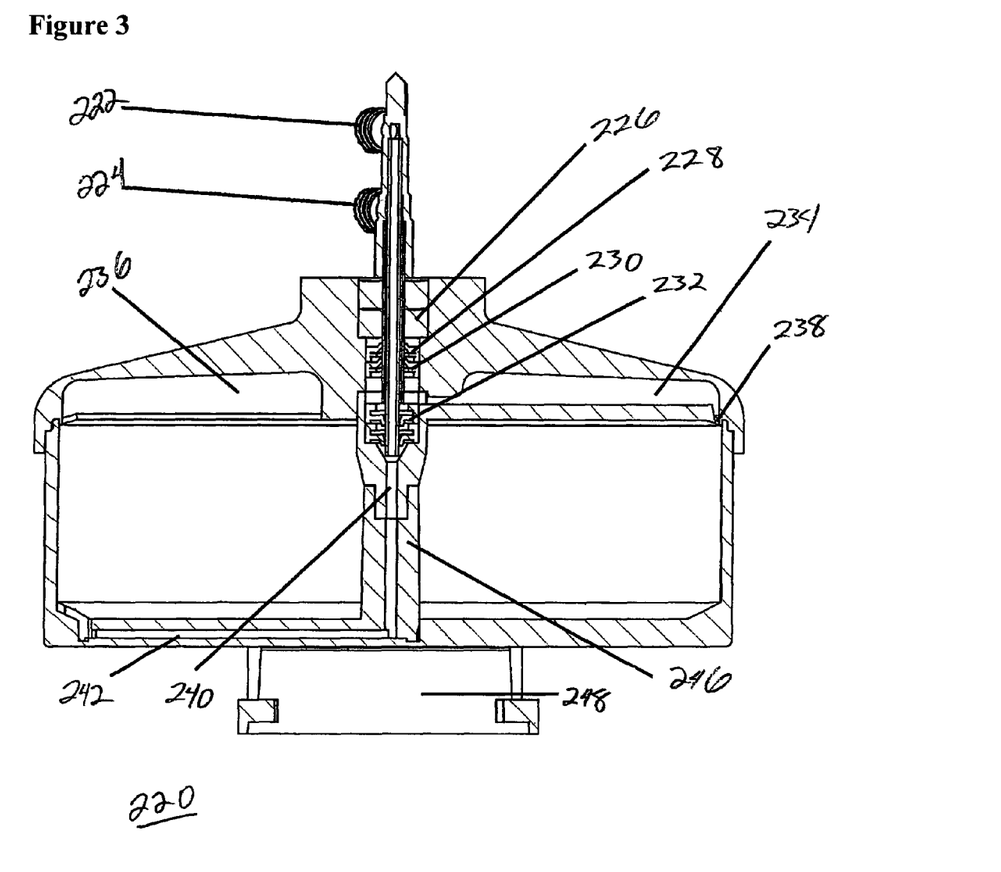
FIG. 3 shows a cross-sectional view of a processing chamber, according to another embodiment of the present invention.
Figure 3A:
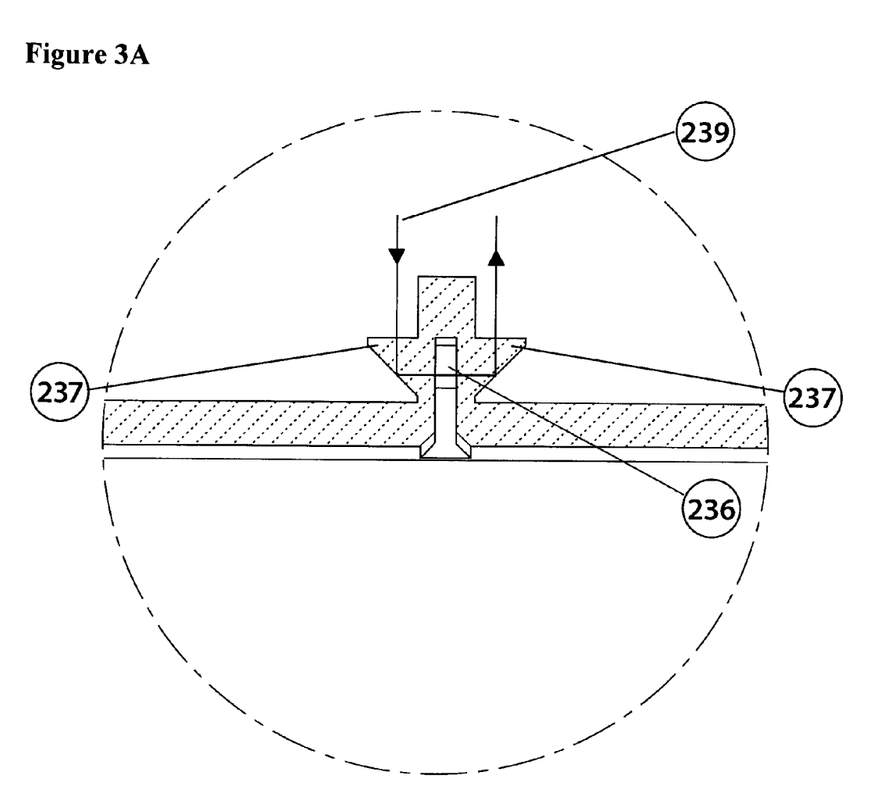
FIG. 3A illustrates a focused view of a portion of a processing chamber as shown in FIG. 3.

FIG. 3 illustrates a cross-sectional view of a chamber according to another embodiment of the present invention. The chamber 220 includes an axis about which the chamber rotates, a central line connect 222 and a outer line connect 224, and one or more internal compartments. Further illustrated are rotational bearing 226, as well as rotational seals 228, 230, 232; inner channel 234, optical detection channel 236 (similar to described above); inner line entry 238 to the chamber; inner line 240, and lower radial channel 242. The chamber further includes an inner reinforcement 246 and a chamber retainer 248. FIG. 3A illustrates a focused view of portion of a chamber 220 is described above. Shown are an optical detection channel 236, a prism 237, and light pass 239 (further indicated by arrows). It can be seen that light from a light source (not shown) is directed by the prism 237 such that is goes through the channel 234 which is filled with sample during centrifugation. The light exiting from the channel 234 is redirected by the prism 237 and can be detected by a detector (not shown).

Figure 4:
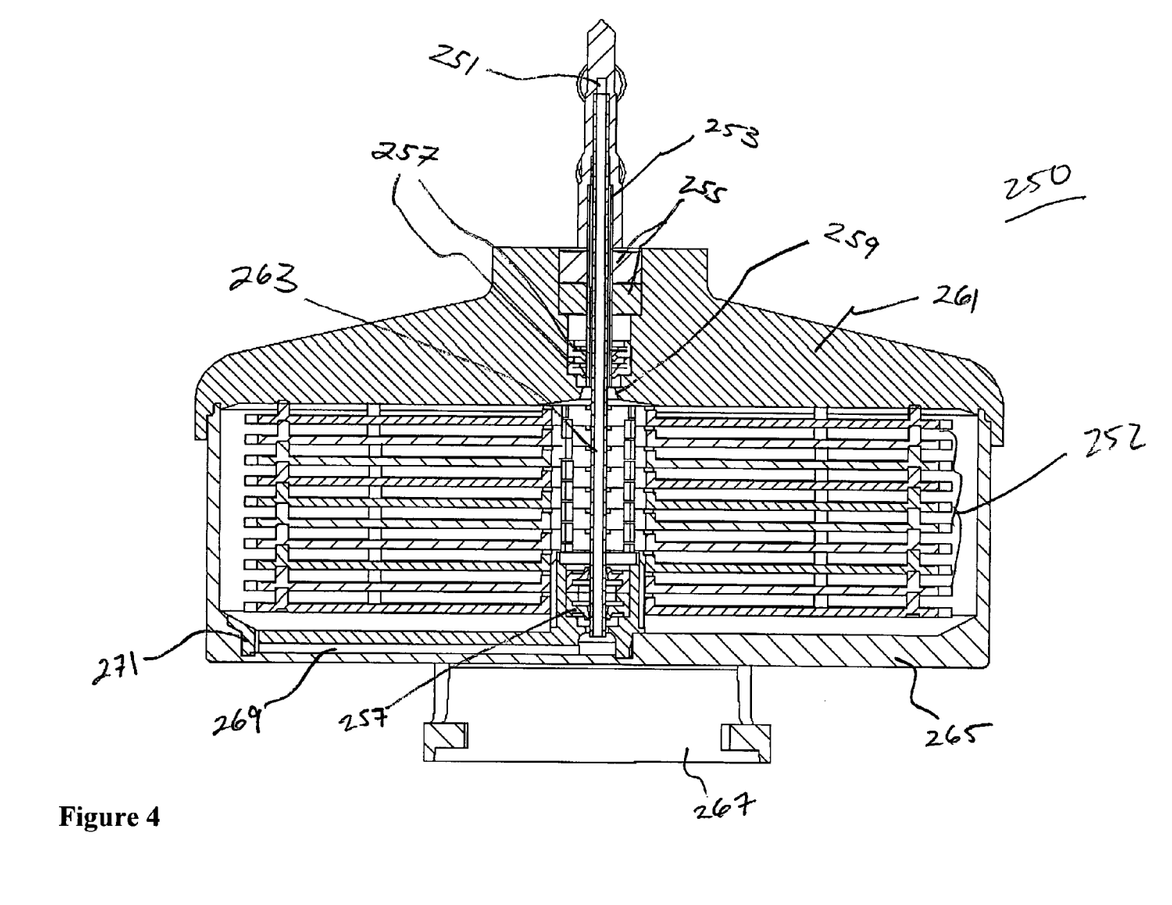
FIG. 4 shows a cross-sectional view of a processing chamber, according to yet another embodiment of the present invention.
Figure 4A:
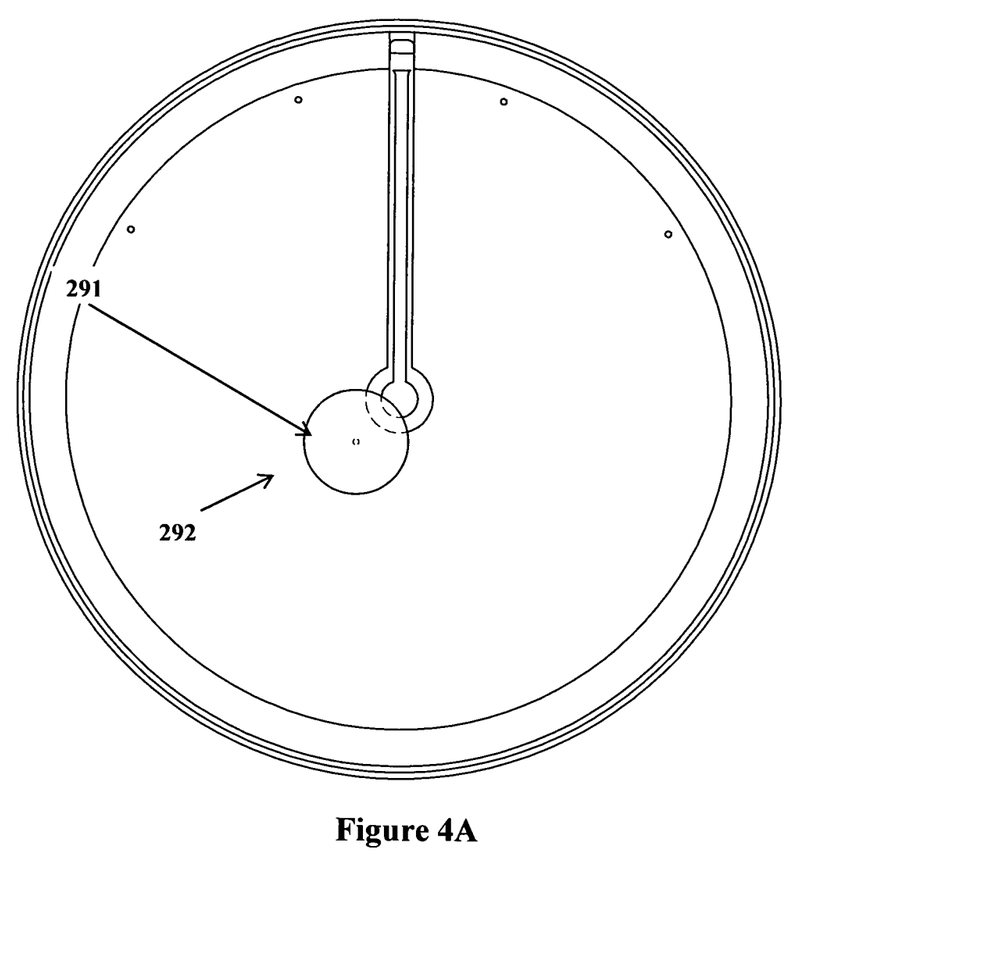
FIG. 4A shows a view over the bottom of the process chamber with opening for gas delivery and a bonded hydrophobic membrane.
Figure 4B:
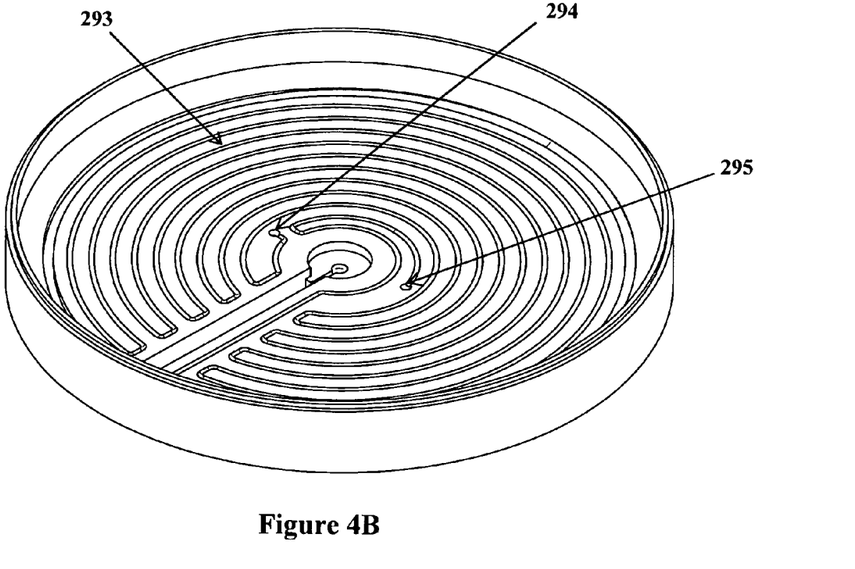
FIG. 4B shows an embodiment of the bottom of the chamber with spiral channels for aeration through membrane bonded to the bottom of the chamber.

In another embodiment of the present invention shown in FIG. 4A, the bottom of the chamber of the centrifuge can possess one or more openings 291 that may be covered with a hydrophobic membrane 292. These openings 291 are used for delivery of gases into the chamber, for instance for cell culture processes (such as $CO_2$, $N_2$, $O_2$, etc.). The membrane can be glued, or bonded thermally or by ultrasound or by other means bonded to the bottom of the chamber in a way to assure sterile connection with the chamber.

In another embodiment of the present invention (FIG. 4B), the bottom of the chamber can possess a system of channels for the gas flow, for instance channels assembled as a spiral system 293, which assures a large contact area between the gases and a membrane bonded over the channels (not shown). The channel system possesses at least one input (opening) 294 and an optional output (opening) 295 for the gases.

The entries or ports of the channels of FIGS. 1-4A may vary in number and location within the channel.

FIG. 4 illustrates a cross-sectional view of a chamber according to another embodiment of the present invention. Construction of chamber 250 is similar in many regards to chambers as described above, but further includes a plurality of layered structures 252. The layered structures 252 can be configured to provide cell culture structures or layers. In use, sample including cells can be introduced into the chamber and flowed over layers 252. Separation processing can include rotation of the chamber such that cells adhering to the layers are separated from those with lesser affinity for the layers. Intermittent rotation and/or breaking during rotation can further disconnect cultured cells from the surface of the layered structures 252 for separation processing. The chamber further includes an illustrated central line 251, outer line 253, bearing 255, rotational seals 257, outer line entry 259 to the chamber, upper portion 261, inner channel 263, base portion 265, retainer 267, lower radial channel 269, and inner line entry 271 to the chamber.

The chamber as described herein may comprise or may be made of various materials. In a preferred embodiment, transparent materials are used like plastics, polystyrol (PS), polysterene, polyvinylchloride, polycarbonate, glass, polyacrylate, polyacrylamide, polymethylmethacrylate (PMMA), and/or polyethylenterephtala (PET). Polytetrafluorethylen (PTFE) and/or thermoplastic polyurethane (TPU), silicone or compositions comprising one or more of the above mentioned materials. The chamber can also be made of polyethylene (PE). In a preferred embodiment, the layers in the chamber comprise or are made of collagen, chitin, alginate, and/or hyaluronic acid derivatives. Possible are also polyactide (PLA), olyglycolida (PGA) and their copolymers, which are biodegradable. Alternatively, non-biodegradable materials can be used, such as polystyrol (PS), polysterene, polycarbonate, polyacrylate, polyethylene (PE), polymethylmethacrylate (PMMA), and/or polyethylenterephtala (PET). Polytetrafluorethylen (PTFE) and for thermoplastic polyurethane (TPU) can also be used. Other alternatives include ceramics and glass materials, like hydroxylapatite (HA) or calcium phosphate. The layers in the chamber can be of solid material or porous.

In a preferred embodiment, the chamber has a size of 2 cm to 50 cm in diameter and a height of 5 mm to 50 cm. Centrifugation is preferentially carried out up to 1000×g. The number of the layers and the distance between the layers is variable. In a preferred embodiment, the chamber can be heated and cooled to provide for a temperature appropriate for the sample to be centrifuged. For this purpose, a heating and/or cooling means can be located at the chamber or surrounding the chamber.

Figure 5:
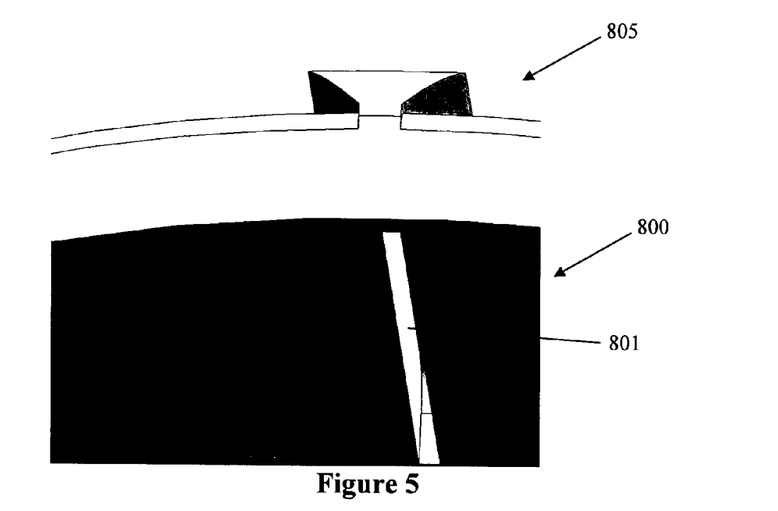
FIG. 5 shows a view of the inside of a lid for a rotating chamber with a channel or gap in which the sample flows during centrifugation, with a means for detecting the progress of separation of the sample in the form of a prism.
Figure 6:
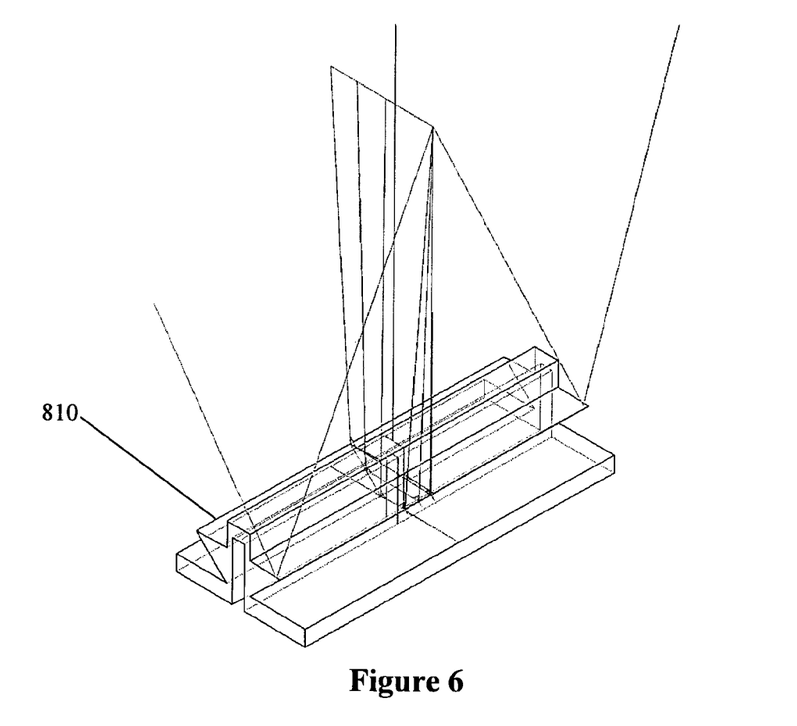
FIG. 6 shows the path of light through the sample by means of a prism. The prism (double prism) is configured such that light from a light source can at least partially penetrate through at least a part of the sample that is being separated through centrifugation, and light passing through at least a part of the sample can be detected by a light detector.
Figure 7:
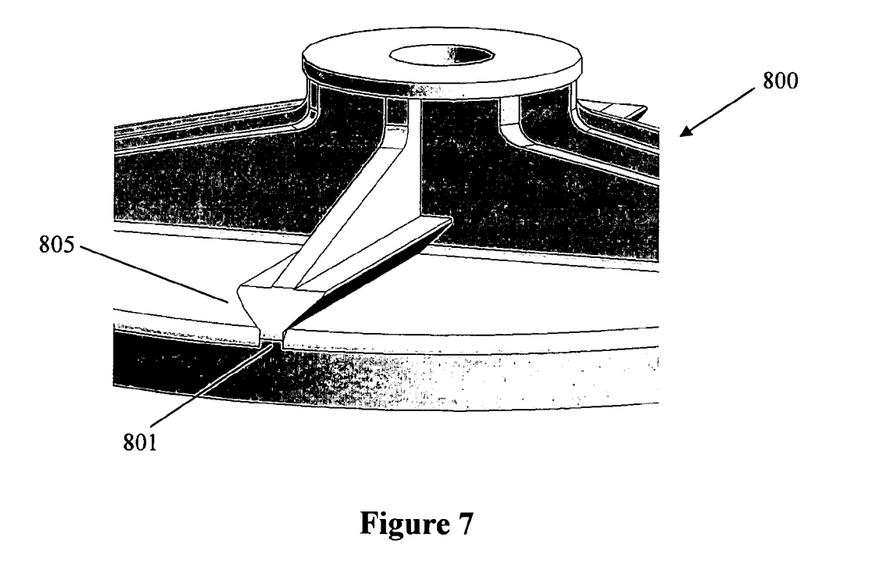
FIG. 7 shows a double prism that is part of a rib located at the lid of the rotating chamber.

The detection of optical layers in the centrifugal chambers is shown in detail in FIGS. 5-7.

The cylindrical shaped centrifuge chamber shown in FIG. 5 is limited on its upper side by a lid 800, which may carry one or more some stabilizing ribs 805 on the flat top surface. At least one of these radial ribs 805 covers a narrow gap or channel 801, open to the centrifuges inner volume when the lid 800 is tied on the centrifuge chamber. The gap 801 extends in axial direction from the inner lid surface passing the lid 800 some millimeters into the rib 805. Therefore, it may be visible from the outside within the rib 805 when transparent material is used. In radial extension, the gap 801 reaches from near the center up to the cylindrical centrifuge wall (FIG. 5).

During centrifugation, the same forces take effect in the gap 801 as in the whole centrifuge chamber. The ring shaped neighbored suspension layers extend parallel into the gap 801 and are displayed as axial standing neighbored thin areas, like a thin layers cross cut, well detectible by external optical sensors.

The gap 801 width can be determined freely, but need to be small enough for a transmitted light analysis of all layer-associated areas in the gap. Thereby, it is possible to quantify the optical densities and colors of all layers of the suspension in the centrifuge chamber in a "touchless" manner from the outside through optical transmission measurements.

To enable a vertical illumination and sensor position to watch the layers movements in the gap, a prism can be added to a rib, e.g. on both rib sides, which may be preformed by the transparent housing material itself.

The prism 810 refracts the vertical generated illuminating beam through the gap (horizontal) and back to the top, vertical again (FIG. 6). During centrifugation, a synchronous position triggered electronic flash light can transmit light into one side of the prism 810, e.g. the left prism, illuminating the gap by refraction. The transmission result is refracted by the other side of the prism 810, e.g. the right prism, back to a vertical mounted camera, possibly in the neighborhood to the upper flash source on the top. The resulting optical sensor unit is easy to handle like a reflex sensor but at the same time allows for full-scale transmission measurements.

The arrangement of the prism's angles ensures the "total reflection" on its inner prism surface for the illuminating flash beams and avoids direct reflections on its outer surfaces between light source and camera. Therefore, there is no need for mirror coatings and injection molding technologies can be used without rework of the facilities being required (FIG. 7).

In one embodiment, the centrifuge of the present invention can be part of a sample processing system, such as known from EP 0 869 838 B1, which is hereby incorporated by reference.

Such sample processing systems that integrate both sample separation systems and sample processing techniques. A system can include a sample processing unit configured to perform certain processing steps prior to separation methods, such as magnetic based separation. As such, the present invention can include a combined sample processing system and sample separation system. Sample processing systems or units can provide sample processing such as cell culturing, washing, preparation, incubation, labeling and the like. Additionally, sample processing systems/units can include centrifugation based separation techniques, where a centrifugal force is applied to a sample so as to separate at least a first component and a second component from a sample.

Thus, a system of the present invention will typically include both a sample processing unit and a sample separation unit. The combined processing/separation system of the invention can include a closed system that can programmed to automatically perform a variety of complex cell processing steps including density based separations, immunoaffinity separation, magnetic including immuno-magnetic separations, cell cultivation/stimulation/activation, washing or final formulation steps. The invention provides a system that minimizes errors of the user, maintains sterility, performs complex cell processing steps with little or no manual interaction, minimizes operator exposure when processing infectious material. Processing at bedside or in surgical room is possible. The device can be operated patient connected e. g. bone marrow obtained from a patient may be processed directly into an input bag of the tubing set. From there, the e.g. bone marrow can be processed, i.e. separated into at least two components.

Figure 8:
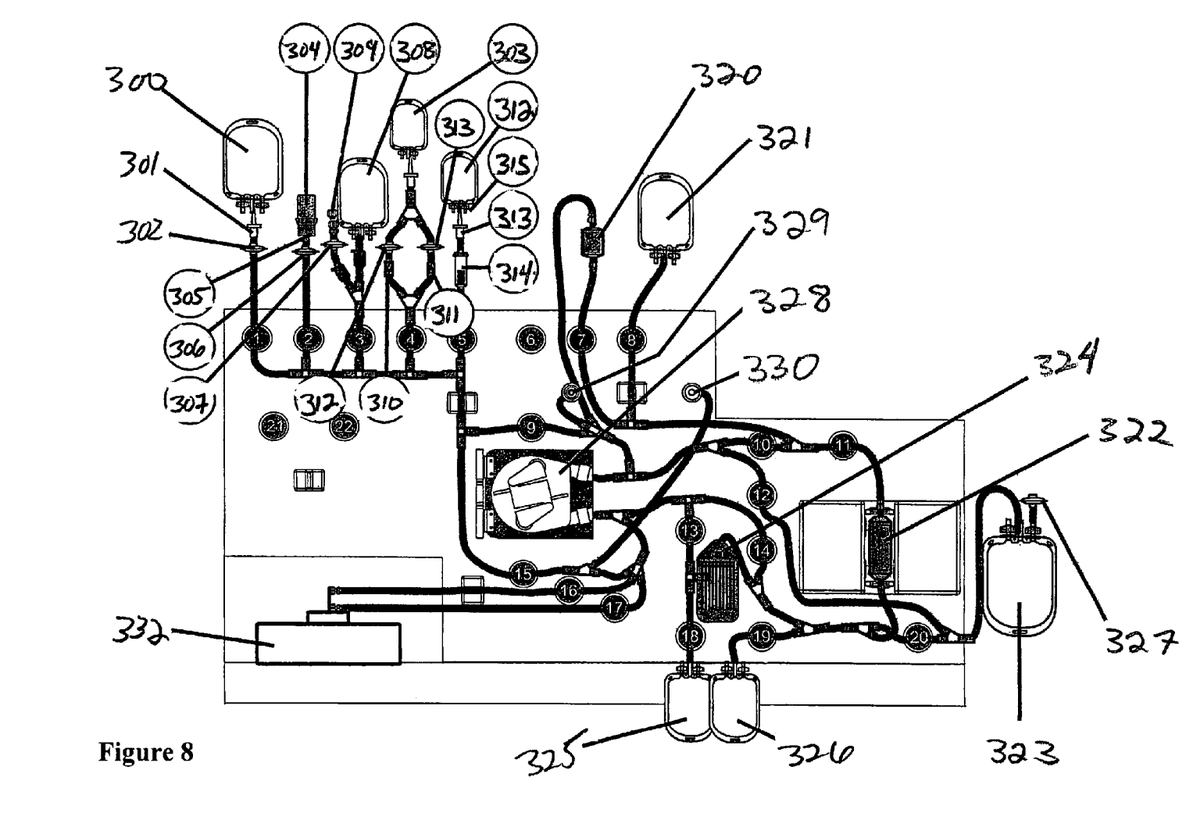
FIG. 8 illustrates a system with a centrifuge according to an embodiment of the present invention.

Accordingly, an embodiment of such a sample processing system is described with reference to FIG. 8. As illustrated, a processing system including various coupled components, flow channels, buffers, reagents, etc. It will be recognized that numerous configurations are available and that the current configuration is provided for illustrative purposes. Referring to FIG. 8, components include a system buffer 300, spike port 301, sterile filter 302, plasma/in process bag 303, magnetic labeling reagent container 304, spike port 305, magnetic reagent sterile filter 306, sterile filter 307, buffer/media bag 308, cell culture media port, auxiliary port 309, single direction valve downwards 310, single direction valve upwards 311, sample bag 312, sample bag connector 313, sample filter 314, sample port 315, filter 316, pre-separation filter 320, in process storage bag 321, magnetic separation column 322, waste bag 323, volume reduction unit 324, positive fraction bag 325, negative fraction bag 326, sterile air filter 327, pump 328, air filter to pressure sensor1 329, air filter to pressure sensor2 330, sample/cell processing unit 332.

EXAMPLE

Cell Culture

The centrifugation chamber of the present invention can be used for culturing of cells, similarly to cell culture flasks or bags.

3.2E5/ml of the human cell line K562 have been applied to a centrifugation chamber in a volume of 30 ml RPMI 1640 cell culture medium supplemented with 10% fetal calf serum. The chamber was placed in a $CO_2$ incubator at 5% $CO_2$. Aliquots of the content have been removed from the chamber for cell counting and viability assessment after 24, 48, and 70 hours. Seeded cells expanded to 4.1E5/ml, 6.4E5/ml and 9.2E5/ml viable cells at 80%, 95% and 95% viability.

The invention claimed is:

1. A centrifuge chamber configured for separating a sample of cells into at least two portions, wherein the chamber comprises:
   (a) a circular base plate, the center of which is substantially perpendicular to a rotational axis of the chamber,
   (b) a cladding which is substantially perpendicular to the base plate,
   (c) a circular cover plate which is positionable on an edge of the cladding that is remote from the base plate,
   (d) an interior configured for processing the sample of cells,
   (e) a chamber window in the base plate or the cover plate through which a part of the sample may be monitored during centrifugation, wherein the chamber window extends radially in the base plate or cover plate from a position near the rotation axis to a position near the perimeter; and
   (f) a detection channel projecting into the base plate or the cover plate from the interior of the chamber to the chamber window, wherein the detection channel is positioned radially from the interior of the chamber to and along the window, and is configured to receive and show the part of the sample through the window during centrifugation;
   wherein the chamber is configured for use in a centrifuge that comprises a detector, wherein the detector is configured and aligned to monitor separation of cells in the part of the sample showing through and along the chamber window.

2. The centrifuge chamber according to claim 1, wherein the chamber window is reflective so as to receive light from a light source, direct the light through the part of the sample that appears in the detection channel, and then redirect light received from the part of the sample to the detector.

3. The centrifuge chamber according to claim 2, wherein the chamber window comprises a prism oriented radially over the detection channel from a position near the rotation axis to a position near the perimeter.

4. The centrifuge chamber according to claim 1, wherein the interior is configured such that the centrifuge chamber can serve as a container for cultivation of cells during centrifugation.

5. The centrifuge chamber according to claim 1, which further comprises at least one layered structure configured for adhering and growing cells thereon.

6. The centrifuge chamber according to claim 1, which is disposable.

7. The centrifuge chamber according to claim 1, which comprises a material chosen from plastics, polystyrol (PS), polystyrene, polyvinylchloride, polycarbonate, glass, polyacrylate, polyacrylamide, polymethylmethacrylate (PMMA), polyethylene terephthalate (PET), polytetrafluoroethylene (PTFE), thermoplastic polyurethane (TPU), silicone, polyethylene (PE), collagen, chitin, alginate, hyaluronic acid derivatives, polylactide (PLA), polyglycolide (PGA) and their copolymers, polystyrol (PS), polysterene, polycarbonate, polyacrylate, ceramics, hydroxyapatite, calcium phosphate, and compositions comprising one or more of such materials.

8. A method for separating a sample into at least two components, comprising providing a sample that can be separated into at least two components, and centrifuging the sample in a centrifuge chamber according to claim 1.

9. The method according to claim 8, further comprising: detecting the progress of separation by detecting the formation of layers of the sample, the change of pH value, and/or the change of temperature.

10. The method according to claim 8, whereby the sample comprises blood cells or bone marrow cells.

11. The centrifuge chamber according to claim 1, wherein the base plate comprises one or more openings for delivery of gases into the chamber during centrifugation.

12. The centrifuge chamber according to claim 1, wherein one or more sensor pads are located on the base plate.

13. The centrifuge chamber according to claim 1, further comprising a sample inlet port and an opening for air or gas, wherein the centrifuge chamber is configured such that the sample can pass through the chamber by way of the sample inlet port, and air or gas to support culturing of cells in the chamber can pass through the chamber by way of the opening, both without stopping centrifugation of the chamber.

14. The centrifuge chamber according to claim 1, comprising a plurality of layered structures that are separate from the base and cover plates and are perpendicular to the rotational axis upon which cells may be cultured.

15. The centrifuge chamber according to claim 14, which is configured such that cells adhering to the layered structures may be separated from cells with lesser affinity for the layered structures.

16. The centrifuge chamber according to claim 14, wherein the layered structures are configured for immunoaffinity separation of cells in the chamber.

17. The centrifuge chamber according to claim 14, wherein the layered structures are configured for magnetic separation of cells in the chamber.

18. The centrifuge chamber according to claim 13, having a system of channels for gas flow assembled in the chamber in a spiral pattern.

19. The centrifuge chamber according to claim 11, further comprising a hydrophobic membrane that is configured to separate gas that has entered the chamber through the one or more openings from sample being processed in the chamber.

20. The centrifuge chamber according to claim 1, further comprising a central line passing into the chamber through and along the rotational axis, and connected to at least one compartment of the chamber, wherein the chamber is configured so that the sample being processed can pass from outside the chamber into or out of the compartment through the central line during centrifugation.

21. The centrifuge chamber according to claim 20, further comprising an outer line that is parallel to and concentric with the central line through and along the rotational axis.

22. The centrifuge chamber according to claim 1, which can be sterilized.

23. A centrifuge comprising:
  (1) a centrifuge chamber according to claims 1; and
  (2) a detector configured and aligned to monitor separation of cells in the part of the sample showing through and along the chamber window.

24. The centrifuge according to claim 23, further comprising a light source configured and aligned to direct an illuminating beam onto the part of the sample that appears in the detection channel through the chamber window during centrifugation, and thereafter to the detector, wherein the detector comprises an optical sensor.

25. The centrifuge according to claim 24, wherein the illuminating beam from the light source is essentially perpendicular to the rotational axis of the chamber.

* * * * *